(12) United States Patent
Schimitzek

(10) Patent No.: US 7,547,247 B2
(45) Date of Patent: Jun. 16, 2009

(54) METHOD OF DETERMINING THE QUALITY AND QUANTITIES OF A BODY OF A SLAUGHTERED ANIMAL

(75) Inventor: Peter Schimitzek, Geilenkirchen (DE)

(73) Assignee: CSB-System AG, Geilenkirchen (DE)

( * ) Notice: Subject to any disclaimer, the term of this patent is extended or adjusted under 35 U.S.C. 154(b) by 440 days.

(21) Appl. No.: 10/579,925

(22) PCT Filed: Nov. 6, 2004

(86) PCT No.: PCT/DE2004/002458

§ 371 (c)(1),
(2), (4) Date: May 19, 2006

(87) PCT Pub. No.: WO2005/055728

PCT Pub. Date: Jun. 23, 2005

(65) Prior Publication Data

US 2007/0178818 A1   Aug. 2, 2007

(30) Foreign Application Priority Data

Dec. 13, 2003   (DE) ............................... 103 58 487

(51) Int. Cl.
*A22C 25/00* (2006.01)
(52) U.S. Cl. ..................................................... 452/157
(58) Field of Classification Search .................... None
See application file for complete search history.

(56) References Cited

U.S. PATENT DOCUMENTS

| | | | | |
|---|---|---|---|---|
| 5,668,634 A | * | 9/1997 | Newman | 356/445 |
| 5,793,879 A | * | 8/1998 | Benn et al. | 382/110 |
| 5,915,279 A | * | 6/1999 | Cantrall et al. | 73/800 |
| 5,944,598 A | * | 8/1999 | Tong et al. | 452/158 |
| 6,735,326 B1 | | 5/2004 | Schimitzek | |
| 6,974,373 B2 | * | 12/2005 | Kriesel | 452/157 |
| 7,039,220 B2 | * | 5/2006 | Kriesel | 382/110 |
| 7,110,572 B1 | * | 9/2006 | Benn | 382/110 |
| 7,128,024 B2 | * | 10/2006 | Doyle, II | 119/518 |
| 7,214,128 B2 | * | 5/2007 | Kriesel | 452/157 |

(Continued)

FOREIGN PATENT DOCUMENTS

DE        298 310        10/1983

(Continued)

*Primary Examiner*—Thomas Price
(74) *Attorney, Agent, or Firm*—Michael J. Striker

(57) ABSTRACT

In a method for the non-invasive determination of the grade, trade value, market value and the quality of a slaughtered animal carcass; based on optical image processing; the method fulfills the conditions of the pertinent official regulations and acts and is rapid and cost-effective to implement; results data of weight percentages from single joint yields that have been obtained during the cutting tests of a sufficient number of slaughtered carcasses are correlated with the characteristic measured values and parameters determined from the ham and loin regions of both sides of a slaughtered animal carcass, taking into consideration the total weight, in order to obtain relationship data; during the slaughter operation, a simulation calculation is then carried out using the existing relationship data to estimate the single joint yields, taking into consideration the total weight of the two sides of a slaughtered animal carcass and the characteristic measured values and parameters that have been determined specifically in the ham and loin regions for said carcass.

16 Claims, 1 Drawing Sheet

U.S. PATENT DOCUMENTS 7,399,220 B2 * 7/2008 Kriesel et al. ............... 452/157

FOREIGN PATENT DOCUMENTS

| DE | 41 09 345 | 9/1991 |
| DE | 41 31 556 | 4/1992 |
| DE | 197 33 216 | 12/1998 |
| DE | 198 47 232 | 12/1999 |
| DE | 198 37 806 | 1/2000 |
| DE | 199 36 032 | 7/2000 |
| DE | 199 52 628 | 5/2001 |
| DE | 100 50 836 | 6/2002 |

* cited by examiner

METHOD OF DETERMINING THE QUALITY AND QUANTITIES OF A BODY OF A SLAUGHTERED ANIMAL

CROSS-REFERENCE TO RELATED APPLICATION

The invention described and claimed hereinbelow is also described in German Patent Application DE 103 58 487.0 filed on Dec. 13, 2003. This German Patent Application, whose subject matter is incorporated here by reference, provides the basis for claim of priority of invention under 35 U.S.C. 119(a)-(d).

BACKGROUND OF THE INVENTION

The invention relates to a method of determining in a non-invasive manner the trade classification, the trade value, the market value and the quality of a body of a slaughtered animal on the basis of optical image processing, which method can preferably be used in slaughterhouses and meat processing works. Generally, larger slaughtered animals, such as pigs, are split along the backbone and suspended on hooks are conveyed by means of special transportation systems between various stations. At predetermined locations the respective halves of the slaughtered pigs are registered, weighed and evaluated.

Within the scope of the evaluation, the body of the slaughtered pig is classified into legal trade classifications on the basis of the muscle-meat percentage. Several methods are permissible for determining the muscle-meat percentage, wherein a measurement of the fat layer (S) and a measurement of the amount of meat (F), measured in each case in millimetres, are set in relation to each other and the muscle-meat percentage (MF %) is calculated by means of an officially established estimating formula.

The values for the terms S and F can be measured in the case of one possible method on a cutlet piece seven centimetres to the side of a line of separation at the level of the $2^{nd}/3^{rd}$ rib. In another conventional method, the two points (ZP) method, in the case of the pig half created by splitting the carcass along the spinal column the amount of fat (S) is determined at the thinnest site of fat over the Musculus Glutaeus Medius (MGM) and the amount of meat (F) as the thickness of the loin muscle, measured as the shortest connection of the front (cranial end) of the MGM to the upper (dorsal) edge of the vertebral canal.

The muscle-meat percentage (MF %) is determined mathematically specifically for Germany by inserting (S) and (F) into the official formula MF %=47.978+(26.0429*S/F)+(4.5154*$\sqrt{F}$)−(2.5018* 1gS)−(8.4212*$\sqrt{S}$)

the value of which is used to determine the trade classification according to the relevant regulations.

The measured values can be determined both manually and also automatically according to the two-point method. A series of documents are known from the prior art and describe the solutions which function automatically for this purpose using optical image processing.

The documents DD 298 310 A5/DE 41 31 556 C2 and DE 41 09 345 C2 describe methods for determining or analysing halves of animal carcasses by means of image processing, wherein the outer contour, layer of fat, meat and back fat ratio are determined, in that images are recorded of the halves of animal carcasses including the backbone and all the intermediate vertebrae layers. As a fixed point for determining the parameters for splitting and classifying the carcass, the starting point is the sacrum of the spinal column, which is also determined in the same way as the other vertebrae by means of object analysis. A disadvantage of this method is on the one hand the high cost of computer technology required to analyse the object using pre-defined contour and object parameters, on the other hand where splitting errors occur during the actual processing, it is not always possible to select the sacrum in a sufficiently reliable manner as a fixed point.

The document DE 197 33 216 C1 describes a method for evaluating halves of slaughtered animals using optical image processing, which renders it possible based on the standard two-point method to classify a carcass using an optical image evaluation of the extended loin region whilst excluding subjective error sources. The accuracy of the estimation for evaluation purposes and thus for classification of the carcass has not been improved thereby in comparison to hitherto known evaluation methods.

A method of evaluating slaughtered animal halves by optical image processing is also known from the document DE 198 47 232 C2, wherein a photogrammetric method is used as a simulation of the conventional two-point evaluation method. In the loin and ham region, two clearly defined points, of which the first point is the body-side end of the pin bone, the second point is the body-side end of the MGM (Musculus Gluteus Medium), and a straight line with the direction of the middle progression of the back fat are recorded photogrammetrically. For actual evaluation purposes, the lengths of partial sections are used which are provided on a perpendicular on the straight line, which is displaced in parallel with the pin bone, at the level of the second clearly defined point through the layer of the back fat. Although in the case of this method the subjective measuring errors of the manually performed two-point method are eradicated, the accuracy of the estimation for evaluation purposes is, however, not substantially increased.

A further method is known from document DE 199 36 032 C1 wherein it is ensured that the quality of halves of slaughtered animals, in particular of slaughtered pigs, is automatically assessed using optical image processing and with respect to the known methods a greater level of reproducible estimating accuracy is achieved which can only be influenced insignificantly by errors during the process of splitting the slaughtered animal and cannot be influenced by optical imaging which is not absolutely perpendicular to the splitting plane, wherein an optical image of the slaughtered animal half in the splitting plane is evaluated in the region of the ham region and loin region photogrammetrically on the basis of specific clearly defined reference points.

The spinal column, the pin bone, the thinnest layer of fat at the MGM and the contours of the back fat in the selected region are used as the clearly defined reference points. The percentage of lean meat which is decisive for assessing the quality is calculated by the summation of part lengths, which are set in ratio with respect to each other and are perpendicular to the straight progression of the canal of the spinal cord in the region of the meat and layer of fat using constants, which are ascertained by means of regression calculations for each term, and a basic constant.

Although within the scope of the method the measured value for the amount of fat (S) is determined in accordance with the legal regulations at correct points, the amount of meat (F) is not determined, as a result of which the muscle-meat percentage (MF %) is not calculated using the official formula, thus classification into the trade classes is not possible.

A method of determining the trade value of the pieces of pig carcasses is known from the document DE 199 52 628 A1, wherein weights, weight and meat percentages of pieces of ham, cutlet, removed cutlet, fillet, shoulder, belly and/or other pieces which can be traded or further processed separately by means of Online—evaluation of pig halves. In order to implement the method, predictors which describe the body structure are determined, which predictors result from the progression of the outer contour of the pig half and, derived therefrom, the area, position and the progression of the spinal column and, derived therefrom, the lengths and areas of part regions of the carcass and one obtained for the pig halves, information regarding the amount of fat and representing the relative thickness and the progression of the approximate total subcutaneous fat layer of the back region. The predictors are set in relation to each other taking into consideration statistical relationships existing between them, as a consequence of which the weight of pieces which are of interest, their weight percentage and meat percentages of the total weight of the carcass are to be determined online in the slaughter line. During the course of the method the complete pig half must be recorded by video and the image object processed and evaluated, which is costly, in order to determine merely the trade value. Owing to the large image region over the entire splitting plane, the rate of evaluation can be impaired and also the weights of pieces cannot be determined in a sufficiently accurate manner.

SUMMARY OF THE INVENTION

The object of the invention is to develop a multi-step method of determining in a non-invasive manner the trade classification, the trade value, the market value and the quality of a body of a slaughtered animal on the basis of optical image processing, which method complies with the conditions of the relevant official rules and regulations and is performed in an accurate, rapid and also cost-effective manner.

The object is achieved by virtue of the features disclosed in patent claims 1 and 2. Preferred developments are evident in the subordinate claims.

The principles of the multi-step method for determining in a non-invasive manner the trade classification, the trade value, the market value and the quality of a body of a slaughtered animal are first to obtain basic data of a body of a slaughtered animal in the actual slaughterhouse as data volumes and then subsequently to perform a simulation calculation for estimating the yield of the individual parts using relational data. These relational data are obtained by correlating percentages of mass of the yield of the individual parts in the result of tests on cut pieces and in parallel thereto with an automatic classification method, which functions with an optical image evaluation of an image of the split animal carcass in the ham region and loin region, of determined characteristic measurement values and parameters.

The entire method with which the quality and quantities of the body of the slaughtered animal are determined consists substantially of three steps which increase in relevance, wherein, however, the results of the individual steps can be determined and demonstrated independently of each other from the data of the optical image evaluation in the imaging region.

European and national regulations for the approval of methods used for classification into trade classes stipulate how to perform the tests on cut pieces of a number of carcasses, in this case carcasses of pigs or their halves. Within the scope of tests on cut pieces according to standard methods the muscle-meat percentage is calculated from the weight of the fillet, the weight of the muscle-meat (including connective tissue) of shoulder, loins boneless, ham and belly, the weight of the cut pieces and the weight of the remaining pieces. These tests on cut pieces are to be recorded including all details.

The accurate documentation includes all relevant data and is available as data volumes which contains with a high level of statistical accuracy the percentage weights of the fluctuating yields of individual parts of non-homogenous bodies of slaughtered animals.

The accuracy of an approved method for automatic classification for estimating the muscle-meat content of the carcasses must for example correspond at least to the level of accuracy which would be achieved in the case of tests on cut pieces from 120 carcasses using a simple regression calculation.

One possible automatic classification method is a known method which determines characteristic measured values and parameters exclusively in the loin and ham region by selecting clearly defined points using optical image evaluation of an image taken of the split side of a carcass half using an optical sensor. These characteristic measured values and parameters, such as lengths, angles and areas and also the brightness and colour information likewise provided with the image are correlated with the result data of the percentage weights of the yields of the individual parts of the tests on cut pieces and relational data are obtained therefrom and stored together with the initial data for subsequent recursive calculations.

Among other things exact measured values for the amount of fat (S) and the amount of meat (F) are determined, wherein the muscle-meat percentage (MF %) of a slaughtered pig are [sic] directly calculated in accordance with the two-point method in Germany using the official formula, thus the classification into the trade class can be performed immediately as the first method step. The classification of pig carcasses using formula specific for the individual country is performed in a similar manner.

As essential basic data of a carcass in the slaughterhouse and processing operation its weight is determined from the total weight of the halves, which have been obtained by splitting along the spinal column and which are hanging on hooks, and the characteristic measured values and parameters in the loin and ham regions are determined by selecting clearly defined points using optical image evaluation of a digital or digitised image taken of the split side of a carcass half using an optical sensor. The clearly defined points are used to determine characteristic values, lengths, angles and areas in the imaging region.

The cutlets are evaluated in the second method step on the basis of determined length measurements of perpendicular part lengths in the region of the straight section of the spinal column in the imaging region with respect to the outer contour and the fat progression and their relationship to each other.

In order to estimate the yield of an individual part the further available characteristic values are used for the simulation calculation by means of a recursive calculation using the relational data from the tests on cut pieces. As the third method step, the total of the piece evaluation thus obtained produces as usual the trade value.

The weight of the carcass forms the basis for estimating the weights of the pieces and from their total in turn the market value is determined.

In this connection it is likewise feasible to estimate the weights of the pieces merely on the basis of the characteristic values, lengths, angles and areas determined in the imaging region, without first determining the total weight of the body of the slaughtered animal and using it in their calculation.

The quality of the carcass is classified with the aid of the brightness and colour information. The advantages of the invention reside particularly in the possibility of using known, non-invasive, automatic methods for determining measured values for determining the muscle-meat percentage (MF %) of slaughtered pigs in accordance with official regulations. It is possible to use both imaging methods which evaluate an image in the splitting plane and also methods for measuring the carcass along the backbone using nuclear spin tomography or computer tomography or ultrasound.

The permissible tolerances for the estimation error for the muscle-meat percentages permissible in accordance with the official specifications are maintained and or not even achieved.

By limiting the imaging region used for evaluation purposes to the ham and loin region it is possible to determine precise measured values and as a consequence to perform more accurate evaluations at a faster rate.

The trade value of the carcass can be determined from the data for the pieces of value. The market value can be calculated taking into consideration the entire mass.

Hitherto known isolated solutions for determining the muscle-meat percentage and where appropriate the trade value can be replaced by the described method in order to be able to determine accurately, rapidly and in a cost-effective manner all parameters for processing, further processing and pricing.

BRIEF DESCRIPTION OF THE DRAWINGS

The invention is explained in detail as an exemplified embodiment with reference to FIG. 1 as an imaging region for determining characteristic measured values and parameters on a half of a carcass.

DESCRIPTION OF THE PREFERRED EMBODIMENTS

Figure 1:

When performing tests on cut pieces from a sufficient number of pig carcasses, in order to obtain the basis data first their weight is determined after killing and cooling, wherein the carcasses can already be split along the spinal column, then a digital image in the loin and ham region is created using an imaging method, the image is then subjected to image analysis and the contour progressions of the meat tissue and fat tissue and bones are detected. Using the contour progressions, individual lengths, distances averaged over contour regions and areas are measured and also brightness and/or colour values are obtained. Subsequently the actual test on cut pieces is performed, the test must be accurately recorded, wherein the weight percentages of all pieces are determined and stored individually.

The parameters and measured values obtained using automatic image analysis are each allocated the weight of the carcass and the weights of the yields of the individual parts, from which specific relational data are calculated. Owing to the comprehensive volume of data collected from numerous tests on cut pieces, these relational data are statistically assured.

The characteristic measured values and parameters in the ham and loin region are obtained during tests on cut pieces and also during active operation in the slaughterhouse using the respective identical method, preferably based on the method described in the document DE 199 36 032 C1. As shown in FIG. 1, in this case an image region 1 of the ham and loin region of a carcass half are recorded with all details and photogrammetrically evaluated.

The image region 1 records in contrast to a dark background the entire width of the ham and loin region with its outer contours 2.1 and 2.2.

Using a histogram analysis the threshold parameters are first renormalised to the respective brightness of the pig carcass with subsequent computerised selection of the different tissue sections on the basis of colour and/or brightness differences in the image region 1. In the usual manner, impurities caused for example by blood are filtered out of the image with the aid of self-checks for consistency.

In the next step, the light-coloured fat is separated from the darker meat and in this manner fat areas 3 and meat areas 4 are determined. Within the meat areas 4, the contour of a Musculus Glutaeus Medium (MGM) 5 is identified using a contour-tracking algorithm and subsequently determining the geometric position. Furthermore, the lower end of the spinal column with vertebrae 6 and a pin bone 7 are visible in the image region 1. In this case, the vertebrae 6 with the vertebrae channel 8 in the straight section of the spinal column are determined using periodicity criteria.

A straight line 9 having the direction of the straight section of the spinal column is placed at the upper (dorsal) edge of the vertebral canal 8 as a starting line for the measurements. A perpendicular 10 is placed on this straight line 9 at the level of a front (cranial) end 11 of the MGM 5, its length of extension as the shortest connection from the front end 11 of the MGM 5 to the upper (dorsal) edge of the vertebral canal 8 corresponds to the meat measurement (F) as the thickness of the loin muscle. The extension of the perpendicular 10 as far as the outer contour 2.2 defines the fat progression over the MGM 5 cranial.

A connection line 12 from the contour of the MGM 5 to the outer contour 2.2 is determined at the level of the thinnest fat layer on the MGM 5 and the length of this extension represents the amount of fat (S).

The muscle-meat percentage (MF %) is calculated online from the two terms (F) and (S), measured in millimetres, in accordance with the two-point method using the specific official formula and is subsequently classified into the trade class on the basis of the determined muscle-meat percentage.

In parallel with the perpendicular 10, further perpendicular lengths 13 can be calculated on the straight lines 9 to the outer contour 2.2, the starting point of which extensions on the straight lines 9 lie in each case in the virtual perpendicular extension of the layer between the vertebrae 6. The perpendicular lengths 13 are cut from an inner contour line 14 of the fat area 3, so that partial lengths are created in the muscle meat and the fat, their lengths are used as fat and muscle lengths and their relationship with each other to evaluate the cutlets 5.

The middle fat layer over the MGM 5, in the region of the area between the extension of the perpendicular 10 as far as the outer contour 2.2 and another perpendicular 15 on the straight line 9 at the level of a rear (caudal) end 16 of the MGM 5 is used to evaluate the ham, it is also used to determine the trade value.

A number of further lengths, angles and areas going beyond the described example are determined in the image region 1, these parameters serve to refine the differentiation of the relational data.

Thus, statements regarding the belly are provided using a middle panniculus adiposus layer 17 in the cutlet region, in the image region 1 from the cranial end 11 of the MGM 5 and regarding the shoulder using ham, cutlet and belly from the other measured values.

The yields of the individual parts are calculated using the data previously obtained from the image analysis and the recorded total weight of the carcass consisting of the two associated halves, which are suspended on hooks, on the basis of the relational data provided in the data volume and this is then used to produce the trade value from the total of the evaluations of the individual pieces and to produce the market value from the total of the weights of the partial pieces.

It is feasible to determine the weight of pieces, such as the ham or the cutlets directly from the measured values of the image analysis.

Furthermore the quality classification is concerned of the carcass and/or pieces is performed with the aid of the brightness and/or colour values available.

A further development of the method which can be used in particular in butchering operations comprises an implemented self-learning effect with the facility to self-check the consistency of the data volume, in that the results of the weighing of pieces performed during processing are compared with the values in the data volume, where appropriate supplemented by further data, by means of which in particular the variance of the results of estimation for the yields of the pieces is further limited.

Data volumes which are expanded and obtained in this manner are used as an upgrade in small slaughterhouses in order for them to achieve likewise even more accurate results of estimation.

All method steps are performed using electronic data processing devices which comprise amongst other things suitable interfaces to imaging devices and weighing devices.

DESIGNATIONS USED

1 Image region
2 Outer contour (2.1; 2.2)
3 Areas of fat
4 Areas of meat
5 Musculus Glutaeus Medius (MGM)
6 Vertebra
7 Pin bone
8 Vertebral canal
9 Straight line
10 Perpendicular
11 Front (cranial) end
12 Connection line
13 Further perpendicular lengths
14 Inner contour line
15 Other perpendicular
16 Rear (caudal) end
17 Middle panniculus adiposus layer

The invention claimed is:

1. A method of determining in a non-invasive manner a trade classification, a trade value, a market value and a quality of a body of a slaughtered animal on a basis of optical image processing, comprising the steps of performing dissection trials from a sufficient number of pig carcasses, in which at first their weight is determined after killing and cooling; creating a digital image in a loin and ham region from a split side of a half carcass as an image region (1) using an imaging method; subjecting the image to an image analysis and contour progressions of a meat tissue and detecting fat tissue and bones; using contour progressions, measuring individual lengths, distances averaged over contour regions and areas, and also obtaining brightness and/or color values as characteristic parameters and measured values; within following dissection trials determining weight percentages of all cuts as individual cuts, comprising a weight of a fillet, a muscle meat of shoulder, loins boneless, ham and belly; a weight of these cuts and a weight of remaining cuts and storing them individually; allocating these characteristic parameters and measured values to a weight of a carcasses and to weights of yields of individual parts from which specific relational data are calculated as basic data; in an ongoing slaughtering operation determining a weight of pig carcasses after killing and cooling; creating a digital image of the image region (1) from the split side of the carcass half in a ham and loin region of the pig by using an optical sensor and subjecting the digital image to image analysis; determining in the image region (1) inside the ham and loin region lengths angles, areas, brightness and/or color information with all details as characteristic parameters and measured values; using a total weight of the carcass and data from results of the previously preformed dissection trials with respect to fluctuating yields of individual cuts of non-homogenous bodies of slaughtered animals; in an active ongoing slaughtering operation correlating the basic data, obtained with dissection trials of a sufficient number of carcasses, of weight percentages from yields of individual cuts, together with characteristic parameters and measured values, including a fat area (3) and meat areas (4), meat measurements (F) and fat measurements (S), part lengths in a muscle meat and fat, a middle fat layer over a MGM (5) in a region of an area between an extension of a perpendicular (10); placing the perpendicular (10) on a straight line (9) at a level of a front (cranial) end (11) of the MGM (5) to an upper (dorsal) edge of a vertebral canal (8) up to an outer contour (2.2) of the ham an loin region, and another perpendicular (15) which is placed on a straight line (9) at a level of a rear (caudal) end (18) of the MGM (5) and stretches up to an outer contour (2.2) and a middle panniculus adiposus layer (17) in a cutlet region determined from two halves of a carcasses of a slaughtered pig in the ham and loin region using a total weight and obtaining relational data therefrom; in an active ongoing slaughtering operation in order to estimate yields of individual cuts performing a simulation calculation with available relational data taking into consideration a total weight of two associated halves of a carcass and determining the characteristic parameters and measured values for this specifically in the ham and loin region.

2. A method as defined in claim 1, further comprising in a part step of an image evaluation in order to perform an online calculation of a muscle meat percentage (MF%) placing a straight line (9) with a direction of a straight section of a spinal column at an upper (dorsal) edge of a vertebral canal (8); and on this straight line creating a perpendicular (10) at a level of a front (cranial) end (11) of a musculus glutaeus medium MGM (5) so that its length of extension as a shortest connection from a front end (11) of the MGM (5) to an upper (dorsal) edge of the vertebrae channel (8) corresponds to a meat measurement (F) as a thickness of a loin muscle; determining at a level of a thinnest fat layer at the MGM (5) a connection line (12) from a contour of the MGM (5) to an outer contour (2.2), with a length of this extension representing an amount of fat (S); calculating the muscle-meat percentage (MF%) online from two terms (F) and (S) in accordance with a two-point method using a formula and subsequently classified into a trade class.

3. A method as defined in claim 1, further comprising in parallel with a perpendicular (10), calculating further perpendicular lengths (13) on the straight line (9) to the outer contour (2.2), with a starting point of each lengths on the straight line (9) lying in a virtually perpendicular extension of a layer between the vertebrae (6); cutting the perpendicular lengths (13) from an inner contour line (14) of a fat area (3) so that part lengths are created in a muscle meat and a fat; using their length as fat and muscle length and using their relationship with respect to each other to evaluate cutlets.

4. A method as defined in claim 1, further comprising determining a weight of cuts, including a ham or cutlets, directly from the measured values of the image analysis.

5. A method as defined in claim 1, further comprising using an average fat thickness over the MGM (5) in a region of an area between an extension of the perpendicular (10) as far as the outer contour (2.2) and another perpendicular (15) on the straight line (9) at a level of a rear (caudal) end (16) of the MGM (5) to evaluate the ham, when determining the trade value.

6. A method as defined in claim 1, further comprising providing statements regarding a belly using a middle panniculus adiposus layer (17) in a cutlet region in the image region (1) from the cranial end (11) of the MGM (5) and a shoulder using ham, cutlet and belly from other measured values (16).

7. A method as defined in claim 1, further comprising when the method is used in butchering operations, using implemented self-learning effect with self-consistency checks on a data volume; and comparing results of weighing of cuts performed during processing with values provided in the data volume and supplemented if necessary with other data.

8. A method as defined in claim 7, further comprising using data volumes expanded by virtue of a self-learning effect as an upgrade in small slaughtering operations.

9. A method as defined in claim 1, further comprising when the method is used in butchering operations, using implemented self-learning effect with self-consistency checks on a data volume; and comparing results of weighing of cuts performed during processing with values provided in the data volume and supplemented if necessary with other data.

10. A method as defined in claim 9, further comprising using data volumes expanded by virtue of a self-learning effect as an upgrade in small slaughtering operations.

11. A method of determining in a non-invasive manner, a trade classification, a trade value, a market value and a quality of a body of a slaughtered animal on a basis of optical image processing, comprising the steps of performing dissection trials from a sufficient number of pig carcasses, in which at first their weight is determined after killing and cooling; creating a digital image in a loin and ham region from a split side of a carcass half as an image region (1) using an imaging method; subjecting the image to image analysis and contour progression of meat tissue, and detecting a fat tissue and bones; using contour progressions measuring individual lengths, distances averaged over contour regions and areas and also obtaining brightness and/or color values as characteristic parameters and measured values; within following dissection trials determining weight percentages of all cuts as individual cuts, including a weight of a fillet, a muscle-meat of shoulder, loins, boneless, ham and belly, a weight of the cuts and a weight of remaining cuts and storing them individually; allocating each of these characteristic parameters and measured values to a weight of the carcass and to weights of yields of individual cuts from a specific relational data are calculated as basic data; determining in an ongoing slaughtering operation a weight of pig carcasses after killing and cooling; creating a digital image of the image region (1) from the split side of the carcass half in a ham and loin region of a pig by using an optical sensor and subjecting the digital image to image analysis; determining in the image region (1) inside the ham and loin region lengths, angles, areas, brightness, and/or color information with all details as characteristic parameters and measured values; using a total weight of the carcass and data from results of previously performed dissection trials with respect to fluctuating yields of individual cuts of non-homogenous bodies of slaughtered animals; correlating in an active ongoing slaughtering operation, basis data obtained with dissection trials of a sufficient number of carcasses, o f weight percentages from yields of individual cuts, together with characteristic parameters and measured values, including fat area (3), meat areas (4), meat measurement (F) and fat measurement (S), part lengths in a muscle meat and a fat, a middle fat layer over an MGM (5) in a region of an area between an extension of a perpendicular (10); placing a perpendicular (10) on a straight line (9) at a level of a front (cranial) end (11) of the MGM (5) to an upper (dorsal) edge of a vertebral canal (8) up to an outer contour (2.2) of the ham and loin region and another perpendicular (15) on the straight line (9) at a level of a rear (caudal) end (16) of the MGM (5) and stretching up to an outer contour (2.2) and a middle panniculus adiposus layer (17) in a cutlet region, determined from two halves of a carcass of a slaughtered pig in the ham and loin region using a total weight and relationship data obtained therefrom; in an active ongoing slaughtering operation in order to estimate yields of individual cuts performing a simulation calculation with available relational data of a carcass; and determining the characteristic parameters and measured values for this in the ham and loin region.

12. A method as defined in claim 11, further comprising in a part step of an image evaluation in order to perform an online calculation of a muscle meat percentage (MF%) placing a straight line (9) with a direction of a straight section of a spinal column at an upper (dorsal) edge of a vertebral canal (8); and on this straight line creating a perpendicular (10) at a level of a front (cranial) end (11) of a musculus glutaeus medium MGM (5) so that its length of extension as a shortest connection from a front end (11) of the MGM (5) to an upper (dorsal) edge of the vertebrae channel (8) corresponds to a meat measurement (F) as a thickness of a loin muscle; determining at a level of a thinnest fat layer at the MGM (5) a connection line (12) from a contour of the MGM (5) to an outer contour (2.2), with a length of this extension representing an amount of fat (S); calculating the muscle-meat percentage (MF%) online from two terms (F) and (S) in accordance with a two-point method using a formula and subsequently classified into a trade class.

13. A method as defined in claim 11, further comprising in parallel with a perpendicular (10), calculating further perpendicular lengths (13) on the straight line (9) to the outer contour (2.2), with a starting point of each lengths on the straight line (9) lying in a virtually perpendicular extension of a layer between the vertebrae (6); cutting the perpendicular lengths (13) from an inner contour line (14) of a fat area (3) so that part lengths are created in a muscle meat and a fat; using their length as fat and muscle length and using their relationship with respect to each other to evaluate cutlets.

14. A method as defined in claim 11, further comprising determining a weight of cuts, including a ham or cutlets, directly from the measured values of the image analysis.

15. A method as defined in claim 11, further comprising using an average fat thickness over the MGM (5) in a region of an area between an extension of the perpendicular (10) as far as the outer contour (2.2) and another perpendicular (15) on the straight line (9) at a level of a rear (caudal) end (16) of the MGM (5) to evaluate the ham, when determining the trade value.

16. A method as defined in claim 11, further comprising providing statements regarding a belly using a middle panniculus adiposus layer (17) in a cutlet region in the image region (1) from the cranial end (11) of the MGM (5) and a shoulder using ham, cutlet and belly from other measured values (16).

* * * * *